(12) United States Patent
Fouche et al.

(10) Patent No.: US 8,609,151 B2
(45) Date of Patent: Dec. 17, 2013

(54) TREATMENT OF ERECTILE DYSFUNCTION AND LIBIDO ENHANCEMENT

(75) Inventors: Gerda Fouche, Pretoria (ZA); Eric Khorombi, Pretoria (ZA); Vinesh Jaichand Maharaj, Pretoria (ZA)

(73) Assignee: CSIR (ZA)

(*) Notice: Subject to any disclaimer, the term of this patent is extended or adjusted under 35 U.S.C. 154(b) by 1232 days.

(21) Appl. No.: 12/302,086

(22) PCT Filed: May 23, 2007

(86) PCT No.: PCT/IB2007/051951
§ 371 (c)(1),
(2), (4) Date: Nov. 24, 2008

(87) PCT Pub. No.: WO2007/138531
PCT Pub. Date: Dec. 6, 2007

(65) Prior Publication Data
US 2009/0202662 A1  Aug. 13, 2009

(30) Foreign Application Priority Data
May 25, 2006 (ZA) .............................. 2006/04334

(51) Int. Cl.
*A61K 31/365* (2006.01)
*A61K 36/185* (2006.01)
*A61K 9/00* (2006.01)

(52) U.S. Cl.
USPC ..................................................... 424/725

(58) Field of Classification Search
None
See application file for complete search history.

(56) References Cited

U.S. PATENT DOCUMENTS 4,486,445 A  12/1984 Patel et al.

FOREIGN PATENT DOCUMENTS

| EP | 1 527 784 A1 | 5/2005 |
| JP | 04-211609 A | 8/1992 |

OTHER PUBLICATIONS

Das et al., *Phytochemistry*, 40 (3), 931-932 (1995).
Ghosal et al., *Phytochemistry*, 13, 1933-1936 (1974).
Horii et al., *Chem. Pharm. Bull.*, 19 (3), 535-537 (1971).
Mosmann, Tim, *J. Immunological Methods*, 65, 55-63 (1983).
Rubinstein et al., *J. Natl. Cancer. Inst.*, 82 (13), 1113-1118 (Jul. 4, 1990).
Apers et al. *Phytochemistry Reviews*, 2 (3), 201-217 (Jan. 2003).
Asano et al., *Phytochemistry*, 42 (3), 713-717 (1996).
Badheka et al., *Phytochemistry*, 25 (2), 487-489 (1986).
Bastos et al., *Planta Modica*, 65, 541-544 (1999).
Burkill, H.M., *The Useful Plants of West Tropical Africa*, p. 167, paragraphs 2,3, edition 2, vol. 2, The Royal Botanic Gardens, Kew (1994).
Chen et al., *J. Nat. Prod.*, 59, 1149-1150 (1996).
Fukamiya et al., *J. Nat. Prod.*, 49 (2), 348-350 (1986).
Horii et al., *Chem. Commun.*, 653-655 (1968).
Levin et al., *J. Andrology*, 18 (3), 246-249 (May/Jun. 1997).
Gonzalez et al., *Tetrahedron*, 34, 1011-1013 (1978).
Okigawa et al., *Tetrahedron*, 26, 4301-4305 (1970).
Siani et al., *J. Nat. Prod.*, 61, 796-797 (1998).
International Search Report PCT/IB2007/051951 (May 22, 2008).

*Primary Examiner* — Terry McKelvey
*Assistant Examiner* — Catheryne Chen
(74) *Attorney, Agent, or Firm* — Leydig, Voit & Mayer, Ltd.

(57) ABSTRACT

A process for the production of a substance or composition for the therapeutic or prophylactic treatment of erectile dysfunction or the enhancement of libido in a male human or animal subject comprises the step of formulating the substance or composition from at least one of plant material and an extract of plant material of at least one plant species of the family Geraniaceae.

20 Claims, No Drawings

TREATMENT OF ERECTILE DYSFUNCTION AND LIBIDO ENHANCEMENT

THIS INVENTION relates to the treatment of erectile dysfunction and to libido enhancement in a male human or animal subject. More particularly, the invention relates to a substance or composition for such treatment; to the use of such substance or composition in the manufacture of a medicament or preparation; to such treatment; to compounds useful for such treatment and to derivatives of such compounds; and to a method of such treatment.

Broadly, the invention provides a process for the production of a substance or composition for the treatment, by therapy or prophylaxis, or erectile dysfunction, and for the enhancement of libido in a male human or animal subject, the process comprising the step of formulating the substance or composition from at least one of plant material and an extract of plant material of at least one plant species of the family Geraniaceae.

The invention also provides the use of a substance or composition in the manufacture of a medicament or preparation for the therapeutic or prophylactic treatment of erectile dysfunction or the enhancement of libido in the male human or animal body, the substance or composition comprising a formulation of at least one of plant material, and an extract of plant material of at least one plant species of the family Geraniaceae.

Examples of such plants include *M. angustifolia, M. alexandraensi, M. attenuate* (syn. *biflora*), *M. brevirostrata, M. belfastensis, M. burkeana* (syn. *glanulata, betschuanica*), *M. depressa, M. deserticola, M. drudeana, M. galpini, M. glandulosissima, M. glauca, M. grandifolia* (syn. Lanceolate), *M. heliotropioides, M. ignea, M. ignorata, M. l'heritieri, M. lanuginose, M. Iongipes, M. luederitziana, M. malvaeflora, M. multifida, M. namaensis, M. natalensis, M. nivea, M. obcordata, M. ovata* (syn. *emarginata*), *M. parvifolia, M. rehmii, M. rudatisii, M. senecioides* (syn. *Praemorsa*), *M. senegalensis* (syn. *trilobata*), *M. speciosa* L, *M. spinosa* (syn. *lobata, pilosa*), *M. stricta, M. transvaalensis*, and *M. umbellata.*

The process may comprise formulating the substance or composition by size reduction into particulate form, e.g. by grinding (which includes milling) and/or cutting, of the plant material in the form of stems and/or roots and/or flowers and/or seeds and/or leaves. The grinding and/or cutting may be of wet plant material, followed optionally by drying thereof, e.g. by oven-drying. Instead, the grinding and/or cutting may be of dried plant material, the process optionally including the step of drying the plant material prior to the grinding and/or cutting. The process may then include packaging the dried ground plant material in porous bags of the nature of tea bags, or formulating the particulate plant material, after the size reduction, into granules, tablets, capsules, oral sprays, creams or lotions. Naturally, the particle size to which the plant material is reduced will be selected in accordance with suitability thereof for the final intended product.

Instead, the formulating may comprise extracting the substance or composition from the plant material by subjecting the plant material, which has optionally been subjected to a prior size reduction, to solvent extraction using a suitable solvent, to obtain a solvent extract containing the substance or composition. Once again, the plant material subjected to the extraction may be wet, or it may be dried, having been subjected to an optional drying step prior to the extraction. If desired, after the extraction, the solvent may be removed to leave a dried extract comprising the substance or composition.

The extract may thus be selected from organic and aqueous extracts. The extract may be selected from organic extracts produced by extraction of plant material with an organic solvent selected from the group consisting of diethyl ether, isopropyl ether, methanol, ethanol, chloroform, dichloromethane, ethyl acetate, hexane and suitable mixtures of two or more thereof or mixtures thereof with water and aqueous extracts produced by extraction of plant material with water. Examples include methanol/dichloromethane mixtures and methanol/water mixtures, respectively in volume ratios, for example, of 1:1 and 9:1.

Instead the extract may be an organic extract produced by extraction of plant material with a supercritical fluid. The supercritical fluid may be supercritical carbon dioxide.

The solvent extract, whether in the form of a solution or after drying, for example by evaporation of organic solvents at atmospheric pressure (including supercritical fluid solvents), at a reduced pressure depending upon ambient temperature and pressure (organic solvents), or by freeze-drying or spray-drying (aqueous solvents), may be refined and/or separated into individual constituents or compounds, using a suitable technique such as solvent/solvent partitioning and/or chromatographic separation.

The process may, as indicated above, include carrying out the solvent extraction on the plant material in finely-divided form, after its having been subjected to size reduction, for the purpose of facilitating subsequent solvent extraction, for example by wet or dry grinding or milling, to have a particle size of at most 6000 µm, preferably at most 5000 µm.

For the purpose of the present invention cold solvent extraction at room or ambient temperature has been found to be adequate at, say 15-30° C., but the invention contemplates that the possibility of hot extraction at elevated temperatures of up to 100° C. is not excluded.

The Applicant has carried out the present process in particular on plants on the species *Monosonia angustifolia* identified as such by the South African National Biodiversity Institute (SANBI) in Pretoria, South Africa. Plants of the genus *Monosonia* are members of the Geraniaceae family, and *M. angustifolia* is a perennial herb with five petalled pink flowers whose geographic distribution is in open grassland throughout South Africa. A herbarium specimen has been deposited at the SANBI in Pretoria under Genspec. No. 39250002. Extracts obtained from *Monosonia angustifolia*, in particular solvent extracts using a methanol/dichloromethane mixture as solvent, have been shown to be promising for the treatment of erectile dysfunction and libido enhancement in male subjects.

Fractionation of organic solvent extracts, such as dichloromethane or 1:1 by volume methanol/dichloromethane solvent extracts for example by solvent/solvent partitioning followed by column chromatography, has isolated five compounds believed to be active in the treatment or prophylaxis of erectile dysfunction and/or libido enhancement. The process may accordingly include isolating active compounds from the extracts, for example by fractionation such as by chromatography, e.g. column chromatography, followed by recombining the active compounds.

The finished product can thus be in the form of a combination of the active compounds and/or the other chemical ingredients that are present in the plant extract. The active compounds may be extracted, as indicated above, by extraction techniques which include aqueous extraction, organic solvent extraction, and super-critical fluid extraction, or related chemical extraction methods, followed by drying (removal of the extracting solvent) by spray-drying, freeze-drying or evaporation. The extract can then be separated by solvent-solvent partitioning coupled with chromatographic separation techniques to give the active compounds. The active compounds can be formulated, for example and in particular, into suitable tablets, capsules and oral sprays.

According to another aspect of the invention, there is provided the use of at least one compound selected from compounds of the formulae (1) and (2)

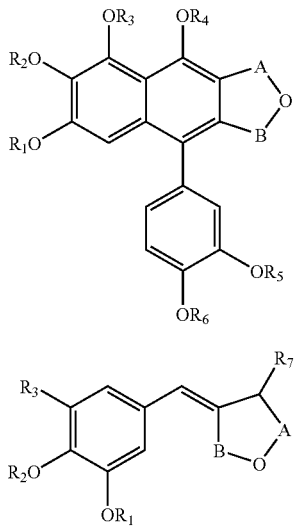

in which $R_1$, $R_2$, $R_4$, $R_5$, $R_6$ are independently selected from H and $C_{1-4}$ alkyl and $R_3$ is independently selected from H and $OC_{1-4}$ alkyl, or $R_1$ and $R_2$ together form $CR_8R_9$ in which $R_8$ and $R_9$ are independently selected from H and $C_{1-4}$ alkyl and $R_3$-$R_6$ are as defined above, or $R_5$ and $R_6$ together form $CR_8R_9$ in which $R_8$ and $R_9$ are independently selected from H and $C_{1-4}$ alkyl and $R_1$-$R_4$ are as defined above, and A is $CH_2$ and B is CO or
B is $CH_2$ and A is CO, and
$R_7$ is $CH_2$-aryl in the manufacture of a medicament for the treatment by therapy or prophylaxis of erectile dysfunction or the enhancement of libido in a male human or animal subject.

$R_1$, $R_2$ and $R_4$-$R_6$ may be selected from Me and H and $R_8$ and $R_9$ may be H.

The $CH_2$-aryl substituent may be

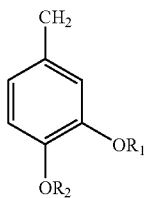

in which $R_1$ and $R_2$ are as defined above.

In particular, the compounds of formula (1) and (2) may be selected from
9-(1',3'-benzodioxol-5'-yl)-4,5,6,7-tetramethoxynaphtho[2,3-c]furan-1(3H)-one (Compound 3)

9-(1',3'-benzodioxol-5'-yl)-4,6,7-trimethoxynaphtho[2,3-c]furan-1(3H)-one (Compound 4)

9-(3',4'-dimethoxyphenyl)-4-hydroxy-6,7-methylenedioxynaphtho[2,3-c]furan-1(3H)-one (Compound 5)

3-(1',3'-benzodioxol-5'-ylmethylene)-4-(3'',4''-dimethoxybenzyl)dihydrofuran-2(5H)-one (Compound 6)

4-(3',4'-dimethoxyphenyl)-9-methoxy-6,7-methylenedioxynaphtho[2,3-c]furan-1(3H)-one (Compound 7)

These compounds are also called 5-methoxyjusticidin A (compound 3), justicidin A (compound 4), chinensinaphthol (compound 5), suchilactone (compound 6) and retrochinensinaphthol methyl ether (compound 7).

The invention extends to a pharmaceutical composition for the therapeutic or prophylactic treatment of erectile dysfunction or the enhancement of libido in the male human or animal body, the composition comprising a formulation of at least one of plant material, and an extract of plant material of at least one plant species of the family Geraniaceae.

The plant material and the extract may be as hereinbefore described.

The invention extends to a pharmaceutical composition for the treatment by therapy or prophylaxis of erectile dysfunction or the enhancement of libido in a male human or animal subject, the composition including at least one compound selected from compounds of formula (1) and (2).

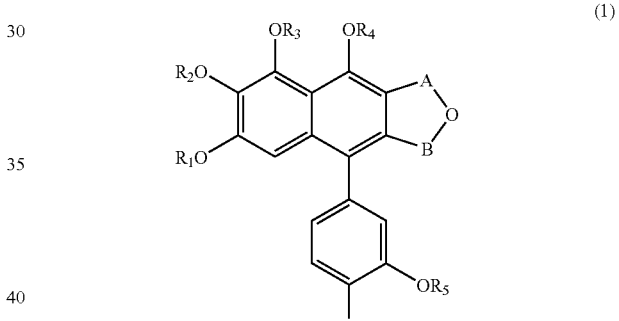

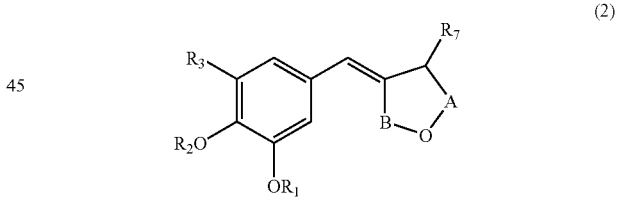

in which $R_1$, $R_2$, $R_4$, $R_5$, $R_6$ are independently selected from H and $C_{1-4}$ alkyl and $R_3$ is independently selected from H and $OC_{1-4}$ alkyl, or $R_1$ and $R_2$ together form $CR_8R_9$ in which $R_8$ and $R_9$ are independently selected from H and $C_{1-4}$ alkyl and $R_3$-$R_6$ are as defined above, or $R_5$ and $R_6$ together form $CR_8R_9$ in which $R_8$ and $R_9$ are independently selected from H and $C_{1-4}$ alkyl and $R_1$-$R_4$ are as defined above, and A is $CH_2$ and B is CO or
B is $CH_2$ and A is CO, and
$R_7$ is $CH_2$-aryl.

$R_1$, $R_2$ and $R_4$-$R_6$ may be selected from Me and H and $R_8$ and $R_9$ may be H.

The CH$_2$-aryl substituent may be

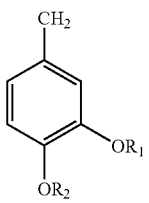

(5)

in which R$_1$ and R$_2$ are as defined in any one of Claims 1 to 3 inclusive.

The compounds of formula (1) and (2) may be selected from compounds (3)-(7).

The structures of compounds 3-7, are set out below

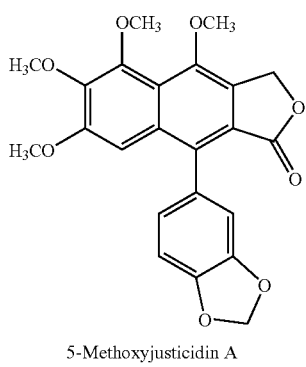

5-Methoxyjusticidin A  (3)

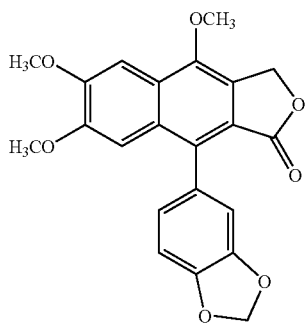

Justicidin A  (4)

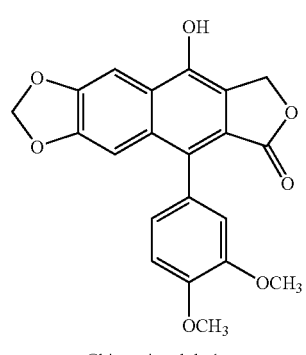

Chinensinaphthol  (5)

-continued

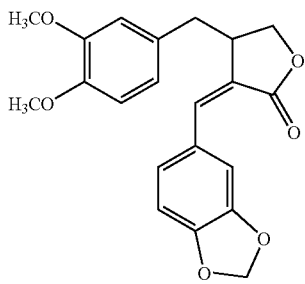

Suchilactone  (6)

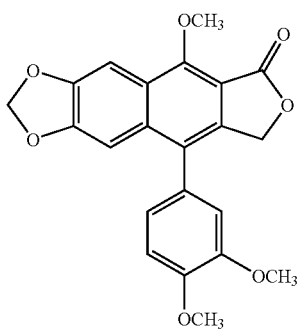

Retrochinensinaphthol methyl ether  (7)

The elucidation of the structures of the isolated Components 3-7, which were isolated by column chromatography from a sample obtained from the plant material of *Monsonia angustifolia* by solvent extraction using a 1:1 by volume material/dichloromethane mixture, followed by drying, partitioning between a 90:10 methanol/water mixture and hexane, then partitioning the methanol/water layer so obtained with dichloromethane and evaporating the dichloromethane layer, was based essentially on spectral analysis. The $^1$H and $^{13}$C NMR (nuclear magnetic resonance) spectral data provided the first stage in the characterization of the compounds. When necessary, advanced homonuclear and heteronuclear two-dimensional NMR methods such as COSY (proton correlation spectroscopy), HMQC (heteronuclear multiple quantum correlation) and HMBC (heteronuclear multiple bond correlation) were applied to achieve the complete assignments of the $^1$H and $^{13}$C correlations of the isolated compounds. From the proton decoupled DEPT (distortionless enhancement by polarization transfer) pulse sequence subspectra, protonated carbons could be assigned according to their multiplicity. The resulting $^{13}$C and $^1$H chemical shift experimental data of the isolated active Compounds 3-7 is collated in Tables 1, 2, 3, 4 and 5 hereunder.

To confirm the so-established structures, the chemical shift data were compared to the data of the previously identified and known compounds on-line or using structural databases. The structures of the five compounds were elucidated as aryl naphthalene lignans which are biosynthetically formed by fusing at least two phenyl propanyl (C6-C3) units. Compound 3 was unambiguously identified as previously isolated from the plant *Justicia procumbens* and is known as 5-Methoxyjusticidin A (Siani, Antonio C et al Journal of Natural Products, 61(6), 796-797, 1998) with a molecular formula C$_{23}$H$_{20}$O$_8$ and a corresponding molecular ion at m/z 424 [M]$^+$. Compound 4 has been identified as Justicidin A with m/z 394 [M]$^+$ (molecular formula C$_{22}$H$_{18}$O$_7$). This compound is one of the most commonly known lignans found in plants (M. Okigawa et al, Tetrahedron, 26, 4301-4305, 1970, L. Badheka et al, Phytochemistry, 25(2), 487-489 1986). Compound 5, is commonly known as Chinensinaphthol and it was previously isolated from *Justicia procumbens* (Z. Horii et al Chemical Communications, 653, 1968). A mass charge of m/z 380 was obtained for this compound, which mass charge is in agreement with the proposed molecular formula of $C_{21}H_{16}O_7$. Compound 6 (molecular formula $C_{21}H_{20}O_6$) was found to have m/z 368 $[M]^+$ and it was assigned the name Suchilactone based on literature and NMR spectral data comparison with the authenticated published data (S. Ghosal et al, Phytochemistry, 13, 1933, 1974, Biswanath Das and Ratna Das, Phytochemistry, 40(3), 931-932, 1995). Compound 7 (molecular formula $C_{22}H_{18}O_7$) was elucidated as Retrochinesinaphthol methyl ether in conjunction with spectral data (Z. Horii et al, Chemical and Pharmaceutical Bulletin, 19(3), 535-537, 1971) and a molecular ion $[M]^+$ of m/z 394 was obtained.

The invention extends to the use of a substance or composition in the manufacture of a medicament or preparation for the therapeutic or prophylactic treatment of erectile dysfunction and for libido enhancement, in the male human or animal body, the substance or composition comprising a formulation obtained from plant material from a plant of the genus *Monsonia*, in particular *Monsonia angustifolia*.

The invention also extends to the use of a substance or composition in the manufacture of a medicament or preparation for the therapeutic or prophylactic treatment of erectile dysfunction and for libido enhancement in the male human or animal body, the substance or composition comprising at least one compound selected from the group consisting of Compound 3, Compound 4, Compound 5, Compound 6 and Compound 7 as identified above.

The substance or composition may comprise a plurality of said Compounds 3, 4, 5, 6 and 7; and for it may comprise one or more derivatives of said Compounds 3, 4, 5, 6, and 7.

The invention also extends to substances and compositions for the treatment, by therapy and prophylaxis, of erectile dysfunction and for libido enhancement in the male human or animal body, the substances or compositions comprising formulations, in particular solvent extracts, (and the active compounds contained therein), obtained from plant material from plants of the genus *Monsonia*.

More particularly, the invention extends to a substance or composition for use in a method of treatment of erectile dysfunction and for libido enhancement, in the male human or animal body, by administering an effective amount of said substance or composition to the human or animal body, said substance of composition forming part of a formulation, in particular a plant extract, obtained from plant material of a plant which is a member of the genus *Monsonia*.

The substance or composition may comprise at least one of Compounds 3-7 identified above or at least one derivative thereof. Preferably the substance or composition comprises all of Compounds 3-7 identified above and, optionally, one or more derivatives thereof.

The invention extends further to a substance or composition for use in a method of treatment by therapy or prophylaxis of erectile dysfunction and for libido enhancement, in the male human or animal body, by administering an effective amount of said substance or composition to the human or animal body, the substance or composition comprising at least one of Compounds 3-7 identified above.

The substance or composition may comprise a plurality of, and preferably all of, said Compounds 3-7, and it may comprise one or more derivatives thereof.

The one or more of Compounds 3-7, or the derivatives thereof, may be present in the substance or composition at a total concentration or proportion of at least 5% by mass, preferably at least 10% by mass and more preferably at least 20% by mass.

In particular the substance or composition may be in a form selected from particles of the plant material which has been subjected to size reduction and contained optionally in porous bags of the nature of tea bags, or in the form of tablets, capsules, oral sprays, syrups and possibly herbal tinctures. Thus, the substance or composition may be for use in a method of treatment or prophylaxis, or a method of enhancement, in which the substance or composition is administered in unit dosage form. Preferably, the administering of the substance or composition is such as to attain an effective total serum concentration by mass of said one or more of Compounds 3-7 identified above, or one or more derivatives thereof, in the human or animal body. More particularly, the administration of the substance or composition may be at an effective daily dosage rate, the rate being dependent on the body mass of the subject.

The invention extends further to novel derivatives of any one of Compounds 3-7 identified above which can be obtained from an extract of a plant of the genus *Monsonia*, in particular *Monsonia angustifolia*.

The invention furthermore extends to a method of treatment by therapy or prophylaxis of erectile dysfunction and to the enhancement of libido, in the male human or animal body, the method comprising administering to a male human or animal subject an effective amount of a substance or composition comprising an extract from a plant of the genus *Monsonia*, in particular *M. angustifolia*.

The invention furthermore extends also to a method of treatment by therapy or prophylaxis of erectile dysfunction and to libido enhancement, in the male human or animal body, the method comprising administering to a male human or animal subject an effective amount of a substance or composition comprising at least one of Compounds 3-7 identified above.

The substance or composition may comprise a plurality, preferably all, of said Compounds 3-7.

The administering of said substance or composition may be in unit dosage form. In particular, the administering of said substance or composition may be such as to attain an effective total serum concentration by mass or one or more of said Compounds 3-5, in the human or animal body. More particularly, the substance or composition may be administered at an effective daily dosage rate, the rate being dependent on the body mass of the subject.

As described in somewhat more detail hereunder, the present invention provides a plant-derived treatment for alleviating erectile dysfunction and for enhancing libido in a male subject. The substances or compositions of the present invention have been demonstrated to be effective in enhancing the libido of male rats in terms of a so-called mating frequency/pregnancy model (MFM). From this enhancement of libido it can be inferred that the substances and compositions of the present invention will also be effective in alleviating erectile dysfunction in a male subject.

The invention will now be described, by way of non-limiting illustrative example, with reference to the following worked Examples:

EXAMPLE 1

Extracts were prepared of plant material from the plant species *M. angustifolia*, identified as such by the SANBI in Pretoria. The plant material comprised the roots, stems, leaves and purple flowers, from which plant material the extracts were prepared.

Initial liquid-liquid partitioning of the extract afforded hexane, dichloromethane and water fractions. Based on PDE 5 inhibition, the dichloromethane fraction showed a 20% improvement in activity compared to the original crude extract. Repeated column chromatography on flash silica gel afforded the isolation of five compounds that were identified as aryl naphthalene lignans 3 to 7, which are formed biosynthetically from two phenyl propanyl (C6-C3) units.

Characterization of 5-methoxyjusticidin A (3)

5-Methoxyjusticidin A (3) was isolated as a white amorphous solid. A molecular ion peak at m/z 425.4 corresponding to [M+1]$^+$ in the positive LRESIMS and at m/z 424 in AutoSpec ETOF EI$^+$ which are both pointing to the molecular formula $C_{23}H_{20}O_8$. The UV spectrum was obtained from a diode array detector (DAD) and absorptions were observed at λ 365, 263 and 237 nm.

In the $^1$H NMR spectra of 3 (Table 1) the presence of a methylenedioxy group, $\delta_H$ 6.02 (1H, d) and $\delta_H$ 6.07 (1H, d) with a very small coupling of J 1.3 Hz was observed. The other methylene singlet observed at $\delta_H$ 5.41 is characteristic of the methylene group found in a penta-lactone ring of lignans. Four singlets assigned to the methoxyl groups were observed at $\delta_H$ 3.74, 3.95, 3.97 and 4.01. An aromatic proton singlet was observed for H-8 at $\delta_H$ 6.94. Three aromatic protons were found exhibiting the ortho coupling (J=7.9 Hz) and meta coupling (J=1.6 Hz) which are consistent with a 1,3,4 trisubstituted phenyl group.

The $^{13}$C NMR spectra showed 23 resonance signals. Four signals could immediately be assigned to the four methoxyl carbons resonating at $\delta_C$ 55.8, 61.4, 62.4, and 62.0. The multiplicity of the other carbon signals was obtained from DEPT spectra that showed 10 protonated carbon signals, two of them being $CH_2$ and four were CH, apart from the four that were already assigned as methoxy groups. There was also evidence of a carbonyl group at $\delta_C$ 169.5, which is characteristic of the lactone functionality in the strained five-membered ring. C-3 was also not found in the aromatic region and was assigned to the methylene group at $\delta_C$ 66.5 attached to the carbonyl forming a lactone. The structure was confirmed by the $^{>1}J_{CH}$ correlations observed in a HMBC experiment.

5-Methoxyjusticidin A 3 was previously isolated by Siani et al. from the wood of *Protium unifoliolatum*[i]. In this article, some of the NMR signals were not assigned correctly (C-9, C-9a, C-8, and C-8a) and we were able to assign them with the aid of 2D experiments. The author acknowledged the wrong assignment and thus the assignment we propose can be taken as correct.

TABLE 1

NMR data* of 5-methoxyjusticidin A (3) in CDCl$_3$

| C | $\delta_C$ | $\delta_H$ (J in Hz) | HMBC $^{>1}J_{CH}$ correlations |
|---|---|---|---|
| 1 | 169.5 | | |
| 3 | 66.5 | 5.41 (s) | C-1, C-4, C-9a |
| 3a | 120.7 | | |
| 4 | 149.1 | | |
| 4a | 122.2 | | |
| 5 | 148.1 | | |
| 6 | 144.9 | | |
| 7 | 153.1 | | |
| 8 | 103.7 | 6.94(s) | C-4a, C-6, C-9 |
| 8a | 133.5 | | |
| 9 | 135.6 | | |
| 9a | 129.9 | | |
| 4-OCH$_3$ | 62.0 | 3.97(s) | C-4 |
| 5-OCH$_3$ | 62.4 | 3.95(s) | C-5 |
| 6-OCH$_3$ | 61.4 | 4.01(s) | C-6 |
| 7-OCH$_3$ | 55.8 | 3.74(s) | C-7 |
| 2' | 101.2 | 6.02, 6.07 (d, 1.4; d, 1.4) | C-7a', C-3a' |
| 3a' | 147.6 | | |
| 4' | 110.6 | 6.78 (d, 1.3) | C-6', C-9, C-7a' |
| 5' | 128.5 | | |
| 6' | 123.6 | 6.75, 6.76 (dd, 1.6, 7.9) | C-4', C-9, C-7a' |
| 7' | 108.3 | 6.92, 6.94 (d, 7.9) | 5', C-3a' |
| 7a' | 147.5 | | |

*$^{13}$C NMR (125.7 MHz) and $^1$H NMR (500 MHz)

Characterization of Justicidin A (4)

This compound was isolated as white amorphous flakes. The $^1$H NMR spectrum of 4 was similar to that of 3. The main difference was that the spectrum of 4 exhibits the presence of only three methoxy groups ($\delta_H$ 3.79, 4.04, 4.11) instead of four as for 3. One methoxy at C-5 was replaced by a proton resonating at $\delta_H$ 7.52. The absence of observed coupling between the two protons resonating at $\delta_H$ 7.52 and 7.04 suggests a para relationship between them. The methylene signal at $\delta_H$ 5.51 which forms part of the furanone ring was still present as was the three aromatic protons that formed the 1,3,4-trisubstituted phenyl group. A pair of proton doublets with very weak coupling ($\delta_H$ 6.02 and 6.06 with a $J_{HH}$ value of 0.9 Hz) was observed for the methylenedioxy substituent.

Twenty two $^{13}$C NMR signals were observed which is in compliance with one less methoxy group. The three methoxy groups were assigned at $\delta_C$ 55.8, 56.1 and 59.7. A carbonyl signal was observed downfield at $\delta_C$ 169.5. The methylene group forming part of the furanone ring was assigned at $\delta_C$ 66.6. The methylenedioxy carbon signal was found at $\delta_C$ 101.2. The rest of the carbon signals were found to support the structural framework with the same substitution pattern as for 5-methoxyjusticidin A (3).

Justicidin A (4) showed a molecular ion peak of m/z 395.4 in ESIMS positive mode corresponding to [M+1]$^+$ and the molecular formula $C_{22}H_{18}O_7$. In the UV spectrum of this compound as obtained from a diode array detector has a strong absorption maximum at 261.7 nm. This compound is widely distributed within the different species of *Justicia* and it has been widely studied before for antiviral[ii], anti platelet[iii,iv] and cytotoxic[v] activity but not for the activity reported here.

Published NMR data for justicidin A[vi,vii] supported the structural assignment of justicidin A (4).

TABLE 2

NMR data of justicidin A (4) in CDCl₃

| C | $\delta_C$ | Dept & HMQC | $\delta_H$ ($J_{HH}$ in Hz) | COSY | HMBC $^{>1}J_{CH}$ correlations |
|---|---|---|---|---|---|
| 1 | 169.5 | C=O | | | |
| 3 | 66.6 | CH₂ | 5.51 | | C-9a, C-4, C-1 |
| 3a | 119.3 | C | | | |
| 4 | 147.8 | C | | | |
| 4a | 126.0 | C | | | |
| 5 | 100.6 | C | 7.52 | | 6-OCH₃ |
| 6 | 151.6 | C | | | |
| 7 | 150.4 | C | | | |
| 8 | 106.2 | CH | 7.04 | | 7-OCH₃ C-4a, C-9, C-6 |
| 8a | 130.7 | C | | | |
| 9 | 134.4 | C | | | |
| 9a | 124.5 | C | | | |
| 4-OCH₃ | 59.7 | OCH₃ | 4.11 | | C-4 |
| 6-OCH₃ | 56.1 | OCH₃ | 4.04 | | C-6 |
| 7-OCH₃ | 55.8 | OCH₃ | 3.79 | | C-7 |
| 2' | 101.2 | CH₂ | 6.02, 6.06 (d, 1.0) | | C-7a', C-3a' |
| 3a' | 147.5 | C | | | |
| 4' | 110.8 | CH | 6.8 (s) | | C-6', C-9, C-7a' |
| 5' | 128.5 | C | | | |
| 6' | 123.6 | CH | 6.76, 6.78(dd, 7.9, 1.4) | H-7' | C-4', C-9, C-7a' |
| 7' | 108.2 | CH | 6.92, 6.94 (d, 7.9) | H-6' | C-5', C-3a' |
| 7a' | 147.4 | C | | | |

*¹³C NMR (125.7 MHz) and ¹H NMR (500 MHz)

Characterization of Chinensinaphthol (5)

Compound 5 is commonly known as chinensinaphthol and it was previously isolated from *Justicia procumbens* and tested for antiplatelet properties as documented by Z. Horii et al 1968.[viii]

A mass to charge ratio (m/z) of 381.4 observed in LRES-IMS in positive mode was assigned to the molecular ion peak [M+1]⁺, which is in agreement with the formula $C_{21}H_{16}O_7$. The UV maximum plot of this compound from the DAD spectrum showed absorptions at 322.0, 266.4 and 228.8 nm, which is characteristic of aryl naphthalene molecules.

Compound 5 was purified by flash silica gel chromatography and visualization under long range UV 254 nm gave a purple coloured spot and a very intense blue fluorescent color when viewed at 366 nm. It was obtained as a white amorphous substance that could not be re-dissolved in a single solvent only. Thus, it was dissolved in a mixture of CDCl₃ and MeOH-d₄ for NMR experiments and the obtained data are collated in Table 6.3.

¹H NMR data showed a singlet at $\delta_H$ 5.35 which can be assigned to the lactone methylene group and a resonance at $\delta_H$ 6.15 (s, H-10) that is characteristic of a methylenedioxy group, and two methoxyl groups appeared as singlets at $\delta_H$ 3.71 and 3.84. In the previous two structures (3 and 4), the methylenedioxy groups were attached to the C ring and the methoxy groups to the A ring. However, $^{>1}J_{CH}$ correlations observed in the HMBC experiment, indicated that in this compound, the methylene group is on the A ring and the methoxy substitutents on the B ring. The three aromatic C ring protons formed an ABX system characteristic of trisubstituted phenyl as it was observed for the lignans 3 and 4. These protons resonated at $\delta_H$ 6.83 (H-2', d, 8.24), 6.77 (H-6', dd, 2.07 & 8.03), 7.05 (H-5', d, 8.24) and their coupling was supported by the COSY 2D correlations.

TABLE 3

NMR data* of Chinensinaphthol (5) in CDCl₃ & CD₃OD

| C | $\delta_C$ | Dept & HMQC | $\delta_H$ (J in Hz) | COSY | HMBC $^{>1}J_{CH}$ correlations |
|---|---|---|---|---|---|
| 1 | 169.4 | C=O | | | |
| 3 | 66.4 | CH₂ | 5.35 (s) | | C-1, C-9a, C-4 |
| 3a | 119.0 | C | | | |
| 4(—OH) | 145.1 | C | | | |
| 4a | 124.6 | C | | | |
| 5 | 97.9 | CH | 7.61 (s) | | C-8a, C-4, C-7 |
| 6 | 148.6 | C | | | |
| 7 | 148.0 | C | | | |
| 8 | 102.5 | CH | 6.85 (s) | | C-4a, C-6, C-9 |
| 8a | 131.0 | C | | | |
| 9 | 130.3 | C | | | |
| 9a | 122.3 | C | | | |
| 10 | 101.9 | CH₂ | 6.15 (s) | | C-6, C-7 |
| 1' | 127.5 | C | | | |
| 2' | 114.2 | CH | 6.83 (d, 2.1) | H-6' | C-4', C-6', C-9 |
| 3' | 148.2 | C | | | |
| 4' | 148.3 | C | | | |
| 5' | 111.2 | CH | 7.05 (d, 8.2) | H-6' | C-1', C-3' |

TABLE 3-continued

NMR data* of Chinensinaphthol
(5) in CDCl$_3$ & CD$_3$OD

| C | $\delta_C$ | Dept & HMQC | $\delta_H$ (J in Hz) | COSY | HMBC $^{>1}J_{CH}$ correlations |
|---|---|---|---|---|---|
| 6' | 122.5 | CH | 6.77 (dd, 2.1 & 8.0) | H-5', H-2' | C-2', C-3', C-9 |
| 3'-OCH$_3$ | 55.5 | OCH$_3$ | 3.71 (s) | | C-3' |
| 4'-OCH$_3$ | 55.4 | OCH$_3$ | 3.84 (s) | | C-4' |

*$^{13}$C NMR (100.6 MHz) and $^1$H NMR (400 MHz)

$^{13}$C NMR spectra data with 21 carbons supported the proposed structure 5 and the mass spectrum data obtained. The carbonyl C-1 of the lactone ring and the methylene group C-3 in the same ring were assigned resonances at $\delta_C$ 169.4 and 66.4 respectively. Other important signals were the two methoxy groups that resonated at $\delta_C$ 55.4 and 55.5 and the methylenedioxy C-10 that resonated at $\delta_C$ 101.9.

On the basis of the spectral data and the supporting correlations observed in 2D NMR experiments, compound 3 was identified as chinensinaphthol.

Characterization of Suchilactone, 6

Crystalline and yellowish 6 was isolated from the methanol-dichloromethane extract of *M. angustifolia* and its spectral data is collated in Table 6.4. The structure was deduced with the help of the 2D NMR correlations that provided information to the C—H connectivity pattern. The proposed structure was also confirmed by comparison to literature data.$^{ix}$ ESIMS (+) of compound 6 showed a molecular ion peak of m/z 368 which agrees with a molecular formula of C$_{21}$H$_{20}$O$_6$. In the mass spectrum, fragments were observed at m/z 151, which was assigned to the fragment 6.1 and at m/z 217 assigned to the fragment 6.2.

Two methoxy groups were observed in the $^1$H NMR spectrum at $\delta_H$ 3.84 and 3.86 as singlets. In contrast to the other compounds where only one 1,3,4-trisubstituted phenyl ring was observed, in the $^1$H NMR spectrum of 6, a second set of ABX protons were present. Additionally, an olefinic proton was observed at $\delta_H$ 7.50.

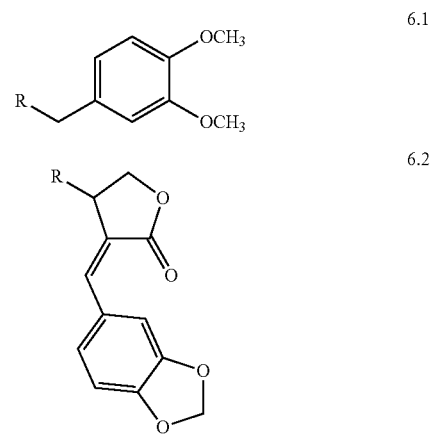

TABLE 4

NMR data* of Suchilactone (6) in CDCl$_3$

| C | $\delta_C$ | $\delta_H$ (J in Hz) | DEPT & HMQC | COSY | HMBC $^{>1}J_{CH}$ correlations |
|---|---|---|---|---|---|
| 2 | 172.5 | | C=O | | |
| 3 | 126.1 | | C | | |
| 4 | 40.1 | 3.75 (m) | CH | H-7", H-5 | C-8', C-2, C-1" |
| 5 | 69.8 | 4.26 (m) | CH$_2$ | H-4 | C-7", C-3, C-2 |
| 2' | 101.7 | 6.02 (d, 1.9) | CH$_2$ | | C-3a', C-7a' |
| 3a' | 148.4 | | C | | |
| 4' | 126.3 | 7.08 (s) | CH | | C-6', C-7a', C-8' |
| 5' | 128.3 | | C | H-6' | |
| 6' | 108.5 | 7.06 (s) | CH | H-7', H-4' | C-4', C-8', C-7a' |
| 7' | 108.8 | 6.87 (dd, 8.5, 1.9) | CH | H-6' | C-5', C-3a' |
| 7a' | 149.2 | | C | | |
| 8' | 137.2 | 7.50 (d, 1.9) | CH | | C-4', C-6', C-2, C-4 |
| 1" | 130.4 | | C | | |
| 2" | 120.9 | 6.73 (dd, 2.0, 8.2) | CH | | C-4", C-6", C-7" |
| 3" | 149.2 | | C | | |
| 4" | 148.1 | | C | | |
| 5" | 111.5 | 6.85 (d, 8.1) | CH | H-6" | C-1", C-3" |
| 6" | 112.2 | 6.69 (d, 2.0) | CH | | C-2", C-4", C-7" |
| 7" | 37.7 | 2.63 (dd, 14.13, 4.31); 3.01 (dd 14.12, 10.02) | CH$_2$ | H-4 | C-3, C-5, C-2", C-6" |
| 4"-OCH$_3$ | 55.9 | 3.86 (s) | OCH$_3$ | | C-4" |
| 3"-OCH$_3$ | 55.9 | 3.84 (s) | OCH$_3$ | | C-3" |

*$^{13}$C NMR (100.6 MHz), $^1$H NMR (400 MHz)

From the COSY correlations it was observed that the protons at H-4 couples with those protons at positions H-5 and H-7". These key correlations are shown in FIG. 6.4 and they are represented by arrows in red. The other correlations observed were H-6' to H-4' and H-7' and also in the C ring there was a strong correlation between H-5" and H6".

The $^{13}C$ NMR of compound 6 showed 21 carbon signals with two methoxy groups overlapping at $\delta_C$ 55.9. The carbonyl in the lactone ring resonates at $\delta_C$ 172.5 and the methylene group in the same ring appears at $\delta_C$ 69.8. The exocyclic double bond of the lactone ring showed resonance peaks at $\delta_C$ 126.1 and 137.2 for the carbons at C-3 and C-8', respectively. The methylene carbon at C-7" was assigned to the signal at $\delta_C$ 37.7. The methylenedioxy group at C-2' showed its resonance peak at $\delta_C$ 101.7. The DEPT spectrum was used to assign the multiplicity of the carbon resonances. Two overlapping methoxy peaks, three $CH_2$ and eight CH peaks, leaving the remaining eight carbon signals to be assigned as quaternary carbon atoms.

Characterization of Retrochinesinaphthol Methyl Ether, 7

Compound 7 ($C_{22}H_{18}O_7$) was identified as retrochinesinaphthol methyl ether.[x] A mass-charge ratio m/z 395.4 $[M+1]^+$ (ESIMS) was obtained which supports the molecular formula of $C_{22}H_{18}O_7$. The structure of the compound is similar to that of 5 with the difference that the methylene and the carbonyl groups of the lactone ring are swapped around and that the hydroxyl group in position C-4 was now replaced by a methoxy group.

yielded 352 g in the 1-2 mm particle size range. To 86 g of the dried plant material was added 1 l of de-ionized water to form a mixture which was boiled for 1 hour. The boiled mixture was allowed to cool to room temperature, filtered and freeze-dried for 24 hours to yield 22.16 g of brownish fluffy powder, forming an aqueous extract.

To 266 g of similarly dried and ground plant material was added 6 l of a 1:1 by volume methanol/dichloromethane mixture, to form a solvent/plant material mixture which was allowed to stand at room temperature for 1 hour with occasional stirring. The solvent/plant material mixture was filtered and the residual plant material was again similarly extracted using a said 1:1 by volume methanol/dichloromethane mixture for 1 hour with occasional stirring. The two filtrates so obtained were combined and evaporated under vacuum at a sub-atmospheric pressure depending upon atmospheric temperature and moisture content to leave 27.32 g of residue, in the form of a sticky dark-green extract.

An amount of 1.5 g of the sticky dark-green methanol/dichloromethane extract was partitioned into two layers between 1 l of a 9:1 by volume methanol/water mixture and 500 ml of hexane. The hexane layer was separated and the methanol/water mixture evaporated at 40° C. to obtain 395.8 mg of a sticky greenish fraction, to which water was added up to a total volume of 500 ml, which was then further extracted using a 500 ml batch of dichloromethane. This dichloromethane batch was separated from the water and the water was then further extracted using a further 500 ml batch of

TABLE 5

NMR data* of compound 7 in $CDCl_3$

| C | $\delta_C$ | Dept & HMQC | $\delta_H$ (J in Hz) | COSY | HMBC $^{>1}J_{CH}$ correlations |
|---|---|---|---|---|---|
| 1 | 169.1 | C=O | | | |
| 3 | 68.8 | $CH_2$ | 5.11 (d, 15.0; d, 15.0) | | C-1, C-4, C-9a |
| 3a | 139.4 | C | | | |
| 4 | 127.5 | C | | | |
| 4a | 135.3 | C | | | |
| 5 | 102.2 | CH | 6.98 (s) | H-8 | C-7, C-8a, C-4 |
| 6 | 148.2 | C | | | |
| 7 | 150.8 | C | | | |
| 8 | 100.2 | CH | 7.71 (s) | | C-4a, C-6, C-9 |
| 8a | 125.3 | C | | | |
| 9 | 155.7 | C | | | |
| 9a | 110.1 | C | | | |
| 10 | 101.8 | $CH_2$ | 6.06 (s) | | C-6, C-7 |
| 9-$OCH_3$ | 63.5 | $OCH_3$ | 4.31 (s) | | C-9 |
| 1' | 128.5 | C | | | |
| 2' | 112.6 | CH | 6.79 (d, 2.0) | H-6' | C-4', C-6', C-4 |
| 3' | 149.4 | C | | | |
| 4' | 149.0 | C | | | |
| 5' | 111.8 | CH | 6.99 (d, 8.0) | H-6' | C-1', C-3' |
| 6' | 121.9 | CH | 6.84, 6.86 (dd, 2.0, 8.0) | H-5', H-2' | C-2', C-4', C-4 |
| 3'-$OCH_3$ | 56.1 | $OCH_3$ | 3.86 (s) | | C-3' |
| 4'-$OCH_3$ | 56.0 | $OCH_3$ | 3.96 (s) | | C-4' |

*$^{13}C$ NMR (100.6 MHz) and $^1H$ NMR (400 MHz)

Comparison of the $^1H$ and $^{13}C$ NMR data of this compound (7) with those reported in the literature[x] and observed for 5 led to the assignment of compound 7 as retrochinesinaphthol methyl ether.

EXAMPLE 2

Plant material from *M. angustifolia* was oven-dried at 35-45° (i.e. 40±5° C.) to more or less constant mass and then ground, to a particle size of 1-2 mm, in a hammer mill. A quantity of 408 g of dried starting material, after milling, dichloromethane which was also separated from the water, and the water was then finally extracted with a final 500 ml batch of dichloromethane which was separated therefrom. The three batches of dichloromethane separated from the water were combined and evaporated at 40° C. to yield 542.6 mg of a brownish extract, while the separated residual water was freeze-dried to yield 473.8 mg of a brownish powder.

A quantity of 6 g of the sticky dark-green diethyl methanol/dichloromethane extract was fractionated and purified using flash chromatography (silica gel 60, Merck, 230-400 mesh) and a 1.5:8.5 by volume ethyl acetate/hexane mixture as eluant to produce 163.6 mg of a steroid β-sitosterol and the Compounds 3-7 identified above, which were lignan compounds and which were respectively produced in quantities of 35 mg (Compound 3), 19.3 mg (Compound 4), 27.2 mg (Compound 5), 36.4 mg (Compound 6) and 16.5 mg (Compound 7).

Methods were tested for the manufacture of a finished product in a form which is suitable for use by humans and intended to be used for the manufacture of a finished dose form. Two methods were used to prepare the products wherein, in one method, fresh wet plant roots, stems, leaves and flowers were cut, boiled in water, filtered and dried to a powder by either spray-drying or freeze-drying. Alternatively the cut plant roots, stems, leaves and flowers were oven-dried by using an oven set to dry at 35-45° C. (i.e. 40±5° C. or by using an herb dryer. The dried plant parts were ground to granules having a particle size of at most 6000 μm and were thereafter extracted by hot water at about 97° C., filtered and dried to a powder using spray-drying or freeze-drying techniques.

In the extraction of the dried plant material 16.00 kg of the stems, leaves and flowers was cut to 5 mm lengths and dried in an herb drier using the drying cycle set forth in Table 6 hereunder. The dry (brownish-green) material was ground to fine granules (3.38 kg having a particle size of at most 6000 μm) and extracted by boiling in 75 l of water for an hour. The water was filtered and the residual plant material was boiled in an additional 75 l water for 30 minutes. The combined filtered water extract (115 l) was left to stand overnight in a cold room. An amount of 500 ml of the water extract was freeze-dried for 24 hours to produce 40.6 g of a dry brownish powder. The remaining 114.5 l was spray-dried (see Table 7 hereunder for the spray-drying conditions employed) and produced 804 g of dry brownish powder which appeared substantially similar to the 40.6 g freeze-dried sample, both visually and chemically. These two extracts were compared by HPLC-MS and TLC methods, which showed them to be similar to each other as well as to the 22.1 g of brownish fluffy powder produced by freeze-drying the aqueous extract described initially.

TABLE 6

Drying parameters for the herb dryer

| | Phase1 | Phase2 | Phase3 |
|---|---|---|---|
| Duration (minutes) | 920 | 920 | 920 |
| Final temperature (° C.) | 35 | 45 | 55 |
| % Relative Humidity | 50 | 45 | 40 |

In the extraction of the fresh wet plant material a combination of the fresh plant stems, leaves and flowers (5.65 kg) was sliced to 5 mm lengths and boiled in 40 l of water for an hour. The water was filtered and the residual plant material was boiled in additional 40 l of water for 30 minutes. The extracts so obtained were combined and filtered to yield 46.62 l of a brownish aqueous extract in the form of a sap. The sap was left in a cold room overnight. Spray-drying (see Table 5 hereunder for spray drying conditions) of the sap generated 242 g of a brownish powder. The powder was shown by HPLC-MS and TLC methods to be similar to the 22.16 g of brownish fluffy powder produced by freeze-drying the aqueous extract described initially, and to the 804 g of brownish powder obtained by spray-drying the aqueous extract of dried plant material described above.

TABLE 7

Spray drying parameters

| Parameters | Aqueous Extract of Dried Plant Material | Aqueous Extract of Wet Plant Material |
|---|---|---|
| Process Gas | 380 K/hr | 380 K/hr |
| Inlet Temperature | 180° C. | 180° C. |
| Outlet Temperature | 88° C. | 95° C. |
| Wall sweep temperature | 80° C. | 88° C. |
| Pneumatic hammers pressure | 1 bar | 1 bar |
| Wall sweep process gas pressure | 1 bar | 1 bar |
| Filter cleaning pressure | 5 bar | 5 bar |
| Atomizer speed | 2600 rpm | 2300 rpm |

A 6.00 g portion of the 804 g of powder which was prepared by spray-drying the aqueous extract of dried plant material as described above was formulated into twenty effervescent tablets at a dose of 300 mg of the spray-dried powder/tablet (see Table 8 hereunder for formulation compositions).

TABLE 8

Ingredients used in the formulation of effervescence tablets

| Item No | Raw Material | Content per dose | Quantity mass or volume |
|---|---|---|---|
| 1. | Spray-dried powder | 300.0 mg | 6.00 g |
| 2. | Colloidal Silicon Dioxide | 15.00 mg | 0.30 g |
| 3. | Aspartame | 20.00 mg | 0.40 g |
| 4. | Cloudifier | 30.00 mg | 0.60 g |
| 5. | Povidone K30 | 80.00 mg | 1.60 g |
| 6. | Sucrose | 954.00 mg | 19.08 g |
| 7. | Citric Acid Anhydrous | 1235.00 mg | 24.70 g |
| 8. | Sodium Bicarbonate | 1360.00 mg | 27.20 g |
| 9. | Tartaric Acid | 350.00 mg | 7.00 g |
| 10. | Polyethylene Glycol 6000 | 80.00 mg | 1.60 g |
| 11. | Ethanol 96% | 5 ml | 5 ml |
| | Total | 4424.00 mg + 5 ml | 88.48 g + 5 ml |

A further 6.00 g portion of the 804 g of powder which was prepared by spray-drying the aqueous extract of dried plant material as described above was formulated into twenty capsules each containing 300 mg of the spray-dried powder. The capsules were produced and contained the ingredients as set forth in Table 9 hereunder.

TABLE 9

Ingredients used in Capsules formulations

| Item No | Raw Material | Purpose | Content per dose | Quantity Mass |
|---|---|---|---|---|
| 1. | Spray-dried Powder | Active | 300 mg | 6.00 g |
| 2. | Micro crystalline cellulose | Filler | 0.060 g | 1.20 g |
| 3. | Green/Red Gelatin Capsules | Capsule | 0.098 g | 1.96 g |
| | Total Mass | | 0.458 g | 9.16 g |

To ascertain the efficacy of the invention, the aqueous and organic extracts described above were tested. A mixture of part of the 22.16 g of brownish fluffy powder initial aqueous extract and part of the 27.32 g of sticky dark-green methanol/dichloromethane extract, prior to the partitioning, was formed by mixing in a ratio of 4:6 by mass and was tested according to the available in vivo sexual activity, mating frequency/pregnancy model (MFM). The model is a measure of male libido. The extract mixture was administered orally to 3 male rats at a dose of 300 mg/kg for 8 consecutive days. Sexual activity was recorded by video surveillance during the nocturnal period i.e. from 17 h 00 to midnight. The vehicle control substance used was distilled water dosed orally to each animal at a daily dose of 10 ml/kg.

The extract mixture exhibited a significant increase in mating frequency and the number of pregnant female rats as compared to the vehicle control, thereby demonstrating increased male libido. The results obtained from the bioassay are shown in Tables 10 and 11 hereunder.

TABLE 10

Results obtained from the Sexual Activity, Mating frequency Assay

| Treatment | Group Number | Day 2 | Day 3 | Day 4 | Day 5 | Day 6 | Day 7 | Day 8 | Total | Mean ± SEM |
|---|---|---|---|---|---|---|---|---|---|---|
| Vehicle | 1 | 13 | 0 | 0 | 0 | 43 | 11 | 1 | 68 | 82.0 ± 10.7 |
| (Distilled | 2 | 42 | 0 | 31 | 1 | 0 | 0 | 1 | 75 | |
| water) | 3 | 38 | 10 | 5 | 0 | 17 | 11 | 22 | 103 | |
| Test | 1 | 39 | 75 | 50 | 48 | 87 | 2 | 0 | 301 | 243.0 ± 55.5 |
| substance | 2 | 6 | 118 | 56 | 74 | 41 | 0 | 1 | 296 | |
| | 3 | 10 | 9 | 11 | 55 | 12 | 17 | 18 | 132 | |

TABLE 11

Results obtained from the Sexual Activity, Pregnancy Assay

| Treatment | Group Number | Individual Number of pregnancies | Total number of pregnancies | Mean ± SEM |
|---|---|---|---|---|
| Vehicle | 1 | 3 | 8 | 2.7 ± 0.3 |
| (Distilled | 2 | 2 | | |
| water) | 3 | 3 | | |
| Test | 1 | 5 | 14 | 4.7 ± 0.3 |
| substance | 2 | 5 | | |
| | 3 | 4 | | |

In order to establish the possible mode of action of the prepared extracts for the MFM activity observed in rats, the extracts were also screened in vitro for inhibition of the phosphodiesterase 5 enzyme. Inhibition of the phosphodiesterase 5 enzyme limits the hydrolysis of cyclic Guanisine Mono-Phosphate (cGMP) to acyclic Guanisine MonoPhosphate (5'GMP) and thereby increases the intracellular concentrations of cGMP which results in the relaxation of the corpus cavernosum smooth muscle. When this muscle is relaxed blood flows and fills the arteries causing the penis to erect.

The aqueous extract and the methanol/dichloromethane extract whose 4:6 by mass combination was the test substance in Tables 6 and 7 above were formed into a different combination by mixing in a 1:1 ratio by mass, which 1:1 combination was tested for the in vitro inhibition of the phosphodiesterase 5 enzyme. It exhibited a significant (80%) inhibition at 100 μg/ml (see Table 12 hereunder).

Further in vitro assaying of part of said 27.32 g of sticky dark-green methanol/dichloromethane extract and of part of the 22.16 g of brownish fluffy powder aqueous extract was carried out separately in the phosphodiesterase 5 enzyme inhibition assay to establish which extract contributed most to the activity of the 1:1 combination. The methane/dichloromethane extract exhibited the highest inhibition of the phosphodiesterase 5 enzyme (see Table 12). It is also worth noting that the enzyme inhibition that was observed from the 1:1 by mass combination was approximately the average of the inhibition observed from the respective methanol/dichloromethane and aqueous extracts and it is measured significant (ie. the results are considered to be significant if more than 50% inhibition is measured).

The assay of the inhibition of the phosphodiesterase 5 enzyme was carried out by the MDS Pharma Laboratory in Taiwan. Phosphodiesterase 5 enzyme, partially purified from human platelets, was used. Test compounds and/or vehicles were incubated with 3.5 μg enzyme and 1 μM cGMP containing 0.01 μM [$^3$H]cGMP in Tris buffer at pH 7.5 for 20 minutes at 30° C. The reaction was terminated by boiling for 2 minutes and the resulting GMP was converted to guanosine by addition of 10 mg/ml snake venom nucleotidase and further incubation at 30° C. for 10 minutes. Unhydrolyzed cGMP was bound to AG1-X2 resin, and remaining [$^3$H]guanosine in the aqueous phase was quantitated by scintillation counting. Compounds were screened at 100 μM. Since enzyme activity could change from lot to lot, the concentration used was adjusted if necessary.

In order to isolate and identify the active ingredients responsible for the inhibitory activity against the phosphodiesterase 5 enzyme, further fractionation through liquid-liquid partitioning was conducted on part of the 27.32 g of sticky dark-green methanol/dichloromethane extract. The dichloromethane, hexane and water fractions obtained therefrom by the partitioning between methanol/water and hexane and further dichloromethane extraction described above were screened for in vitro phosphodiesterase 5 enzyme inhibition. Only the dichloromethane fraction resulted in a substantial increase in the inhibition of phosphodiesterase 5 enzyme relative to the crude plant extracts.

TABLE 12

Summary of results demonstrating inhibition

| Test sample | Concentration μg/ml | % Inhibition of the phosphodiesterase 5 enzyme |
|---|---|---|
| Aqueous extract | 100 | 68 |
| Methanol/dichloromethane extract | 100 | 96 |
| Aqueous + methanol/dichloromethane extract mixture (1:1 by mass) | 100 | 80 |

TABLE 12-continued

Summary of results demonstrating inhibition

| Test sample | Concentration µg/ml | % Inhibition of the phosphodiesterase 5 enzyme |
|---|---|---|
| Dichloromethane fraction | 100 | 101 |
| Hexane fraction | 100 | 62 |
| Water fraction | 100 | 85 |

As the inhibition of the phosphodiesterase 5 enzyme is one of the mode of actions that may facilitate the relaxation of the corpus cavernosum smooth muscle, part of the 22.16 g of the brownish fluffy powder aqueous extract and part of the 27.32 g of sticky dark-green methanol/dichloromethane extract were also tested for the relaxation of the pre-contracted rabbit corpus cavernosal smooth muscle.

Measurement of rabbit corpus cavernosum smooth muscle relaxation/contraction was assayed by the University of Pretoria Assay Laboratory in Pretoria, South Africa in accordance with the bioassay as described by Levin et al. 1997 Journal of Andrology, Volume 18, No. 3, pages 246-249 (with some minor changes). Strips (12 mm long and 1-2 mm thick) of rabbit corpus cavernosal smooth muscle were dissected and mounted in an organ-bath chamber containing Krebs-PSS solution with the following composition: NaCl=7.01 g/l, KCl=0.34 g/l, KH2PO$_4$=0.1 g/l, NaHCO$_3$=1.99 g/l, CaCl$_2$=0.2 g/l, MgSO$_4$=0.3 g/l and glucose=1.8 g/l. One end of the muscle was tied to the inside bottom of the perfusion bath and the other end to a thin wire connected to a Harvard isotonic force transducer for isotonic tension measurements. Changes in isotonic tension were recorded on a computerized calibrating program. The corpus cavernosum muscle was perfused with 2 ml Krebs-PSS buffered saline solution and oxygenated with 95% O$_2$ and 5% CO$_2$ for 5 minutes to establish a stable base-line recording. This was followed by perfusion with 2 ml of high CaCl$_2$ in Krebs-PSS (17.8 mg/ml) for muscle contraction. Base-line tension was set at the point of maximal contraction following the addition of CaCl$_2$ into the experimental bath. The extracts to be analyzed were added after a stable contraction base-line. The same procedure was repeated for the positive control, Sildenafil. The contraction/relaxation was reported relative to Sildenafil tested at 78 ng/ml. In these experiments the stimulation frequency used for rabbit strips was 9 Hz. Both of these extracts demonstrated a potential to relax the rabbit corpus cavernosum smooth muscle with the aqueous extract demonstrating this potential more significantly than the methanol/dichloromethane extract (see Table 13 hereunder).

TABLE 13

Results obtained from the assaying of extracts in the rabbit corpus carvernosal smooth muscle assay.

| Test sample | Concentration of sample (mg/ml) | Relax (R)/Contraction (C) % (standard deviation in brackets) |
|---|---|---|
| Aqueous extract | 2.6 | 50 (0) R |
| Methanol/dicholormethane extract | 2.6 | 46 (7.1) R |

Viagra showed 100% smooth muscle relaxation at $1.8 \times 10^{-5}$ mg/ml

Although the aqueous extract showed more significant relaxation of the smooth muscle as compared to the methanol/dichloromethane extract, the difference was not conclusive. However the latter exhibited a higher phosphodiesterase 5 enzyme inhibition than the former (see Table 12 above). The significant phosphodiesterase 5 enzyme activity shown by the methanol/dichloromethane extract necessitated further investigation, by chromatographic purification thereof in order to isolate the components responsible for the observed activity.

Fractionation of the methanol/dichloromethane extract resulted in the isolation of Compounds 3-7, all of which were shown to be lignans as illustrated above. The five lignans were also shown to be present in the dichloromethane fraction using thin layer chromatography (TLC) and HPLC methods. These lignans were screened for phosphodiesterase enzyme inhibition as described above by MDS Pharma, they were screened as described hereunder for the relaxation of the pre-contracted rabbit smooth muscle and they were screened as described hereunder for cytotoxicity against the Chinese hamster ovarian cells (CHO) the results of which are summarized in Table 14 hereunder.

Rabbit corpus cavernosum relaxation/contraction was measured by the MDS Pharma Laboratory. Corpus cavernosum obtained from New Zealand-derived albino male rabbits weighing 2.5-3 kg and sacrificed by CO$_2$ overexposure was used. A strip from the basal area of the corpus cavernosal was removed and placed under 2 g tension in a 10 ml bath containing Krebs solution at pH 7.4 at 32° C. and sub-maximal isometrically recorded tonic contraction was induced by phenylephrine (3 µM). The test substance (30 µM) induced relaxation by 50% or more (>50%) within 5 minutes, relative to the control 0.3 µM sodium nitroprusside response, indicating significant relaxation.

In vitro cytotoxicity against mammalian cell line was assayed against Chinese hamster ovarian cells by the Assay Laboratory of the Department of Medicine, Division of Pharmacology, University of Cape Town, South Africa.

Samples of Compounds 3-7 were tested for in vitro cytotoxicity against the Chinese Hamster Ovarian cell line using the 3-(4,5-dimethylthiazol-2-yl)-2,5-diphenyltetrazolium-bromide (MTT) assay. All samples were tested in triplicate on a single occasion. The MTT-assay was used as a calorimetric assay for cellular growth and survival, and compares well with other available assays (Mosman, Journal of Immunological Methods 65, 55-63 (1983) and Rubinstein et al., Journal of the National Cancer Institute 82, 1113-8 (1990)). The tetrazolium salt MTT was used to measure all growth and chemosensitivity.

Aqueous samples were dissolved in water and organic samples were dissolved in a methanol:water mixture (1:9) by volume. The initial concentration of stock solutions was 2 mg/ml for all samples. Samples were stored at −20° C. until use. The highest concentration of methanol to which the cells were exposed to had no measurable effect on the cell viability (data not shown). Emetine was used as the positive control in all experiments. The initial concentration of emetine was 100 µg/ml, which was serially diluted in complete medium with 10-fold dilutions to give 6 concentrations, the lowest being 0.001 µg/ml. The same dilution technique was applied to all other samples with an initial concentration of 100 µg/ml to give 5 concentrations, with the lowest concentration being 0.01 µg/ml.

The 50% inhibitory concentration (IC$_{50}$) values for these samples were obtained from dose-response curves, using a non-linear dose-response curve fitting analyses via GraphPad Prism v.2.01 software.

TABLE 14

Bioassay results for Compounds 3 to 7

| Compound No. | Phosphodiesterase 5 enzyme inhibition (%) at 10 μM | Smooth Muscle relaxation (%) at 30 μM | Chinese hamster ovarian cell test IC50 (μg/ml) | Molecular Formula |
|---|---|---|---|---|
| 3 | 11 | 62 | 9.0 | $C_{23}H_{20}O_8$ |
| 4 | 22 | 0 | 1.0 | $C_{22}H_{18}O_7$ |
| 5 | 29 | 75 | 28.5 | $C_{21}H_{16}O_7$ |
| 6 | 35 | 71 | >100 | $C_{21}H_{20}O_6$ |
| 7 | 53 | 57 | >100 | $C_{22}H_{18}O_7$ |

Phosphodiesterase 5 enzyme inhibition and smooth muscle relaxation were considered significant at ≥50% values IC50 values ≤1.0 are considered to be cytotoxic in Chinese hamster ovarian cell tests, Emetine was used as the control with an $IC_{50}$ value of 0.04 μg/ml
Viagra showed 100% relaxation at $1.8 \times 10^{-2}$ μg/ml or an $IC_{50}$ value of $4.1 \times 10^{-3}$ μM for phosphodiesterase 5 enzyme inhibition Significant inhibition was obtained for Compound 7 in the phosphodiesterase 5 enzymatic assay. Rabbit corpus cavernosum smooth muscle relaxation was observed for Compounds 3, 5, 6, and 7. The results indicate that, while these compounds demonstrated significant relaxation of the rabbit corpus cavernosum smooth muscle, their ability to inhibit the phosphodiesterase 5 enzyme was limited (except for Compound 7). This indicates that the Compounds 3, 5, 6 and 7 could act through a different mode of action. In addition the whole plant extract may act by inhibiting the phosphodiesterase 5 enzyme through a synergistic effect.

The isolated lignan compounds were also tested for cytotoxicity against the Chinese hamster ovarian cells (Table 14 above) and Emetine was used as the control with an $IC_{50}$ value of 0.04 μg/ml (values ≤1.0 are considered to be cytotoxic). The four Compounds 3, 5, 6, and 7 that have relaxation effect on the pre-contracted rabbit smooth muscle are non-cytotoxic at the test concentrations with the least toxic being Compounds 6 and 7. The cytotoxic Compound 3 according to this Chinese hamster ovarian cell test, did not exhibit any relaxation of the rabbit smooth muscle and demonstrated an insignificant inhibition of the phosphodiesterase 5 enzyme at the Compounds' test concentrations. Thus Compounds 3, 5, 6 and 7 have a therapeutic window of interest based on the evaluated concentrations.

EXAMPLE 3

Extracts of *M. angustifolia* were compared with extracts of *M. galpinii* and *M. brevirostrata* to show the presence of compounds (3)-(7) in these plants. The results are shown in Table 15.

Method of Extract Preparation:

The dried plant material was ground and successively extracted with methanol-dichloromethane (1:1, v/v). The solvent was filtered and evaporated to dryness in a rotary evaporator in vacuo. The generated organic extracts were stored in a cold room at −20° C. when not in use.

HPLC Analysis:

Sample Preparation:

Samples were reconstituted in a 50:50 methanol:acetonitrile mixture, vortexed for 30 seconds, filtered and injected. Romil methanol and acetonitrile were used throughout.

HPLC Method:

Waters 2695 HPLC Pump:
Solvent gradient:

| Time (min) | % 10 mM Formic acid in Acetonitrile | % 10 mM Formic acid in water | % Acetonitrile | Flow rate |
|---|---|---|---|---|
| 0.0 | 35.0 | 65.0 | 0.0 | 0.20 |
| 5.0 | 35.0 | 65.0 | 0.0 | 0.20 |
| 20.0 | 45.0 | 55.0 | 0.0 | 0.20 |
| 25.0 | 95.0 | 5.0 | 0.0 | 0.20 |
| 30.0 | 0.0 | 0.0 | 100.0 | 0.30 |
| 34.0 | 0.0 | 0.0 | 100.0 | 0.30 |
| 35.0 | 35.0 | 65.0 | 0.0 | 0.25 |
| 45.0 | 35.0 | 65.0 | 0.0 | 0.20 |

| | |
|---|---|
| Column | Hypersil Gold Dim 150 × 2.1 mm, 3μ particle size. |
| Column Temperature | 40° C. |
| Detection: | |
| UV conditions: | |
| Waters 996 PDA | |
| Start wavelength (nm) | 200 |
| End Wavelength (nm) | 450 |
| Resolution (nm) | 1.2 |
| Sampling rate | 1.00 spectra per second |
| MS conditions: | |
| Micromass Quattro LC | |
| Cone (Volts) | 25 |
| Scan Time (secs) | 1.50 |
| Inter scan delay (secs) | 0.10 |
| Mode | ESI+ |
| Full scan | 100-600 m/z (Centroid) |
| Source (° C.) | 120 |

TABLE 15

| | Chinensinaphthol (5) | Suchilactone (6) | Justicidin A (4) | Retrochinensinaphthol methyl ester (7) | 5-methoxyjusticid A (3) |
|---|---|---|---|---|---|
| | | | Retention time | | |
| | 10.4 | 15.9 | 18.8 | 22.9 | 25.07 |
| | | | M + 1 | | |
| Samples | 381 | 369 | 395 | 395 | 425 |
| M. angustifolia | present | present | present | present | present |
| M galpinii | present | present | present | Not present | Not present |
| M brevistrata | present | present | present | present | present |

15

The present invention can, at least potentially, be regarded as having the following beneficial properties:

a) A treatment for the erectile dysfunction as well as for increasing male libido is provided;
b) Extracts of the plant that induce the relaxation of the pre-contracted corpus cavernosum smooth muscle demonstrate a potential treatment for erectile dysfunction;
c) Compounds 3, 5, 6, and 7 isolated from the extracts of the plant demonstrate a potential for the treatment of erectile dysfunction through relaxation of the pre-contracted corpus cavernosum smooth muscle without inhibition of the phosphodiesterase 5 enzyme, thereby reducing any unwanted side effects which may occur through the inhibition of this enzyme; and
d) The extracts and compounds for the treatment of both erectile dysfunction and for increasing male libido.

REFERENCES i. Siani, A. C., Zoghbi, M. das G. B., Wolter, E. L. A. and Vencato, I., 1998. *J. Nat. Prod.,* 61, 796-797.
ii. Asano, J., Chiba, K., Tada, M., and Yoshii, T., 1996. *Phytochemistry,* 42, 713-717.
iii. Gonzalez, A. G., Perez, T. P. and Trujillo, J. M., 1978. *Tetrahedron,* 34, 1011-1013.
iv Chen, C., Hsin, W., Ko, F., Huang, Y., Ou, J. and Teng, C., 1996, *J. Nat. Prod.* 59, 1149-1150.
v. Fukamiya, N. and Lee, K., 1986. *J. Nat. Prod.* 49, 348-350.
vi. Okigawa, M., Maeda, T. and Kawano, N., 1970. *Tetrahedron,* 26, 4301-4305.
vii. Badheka, L. P., Prabhu, B. R. and Mulchandani, N. B., 1986. *Phytochemistry,* 25, 487-489.
viii. Horri, Z., Ohkawa, K., Kim, S, and Momose, T., 1968. *Chem. Commun.,* 653-655.
ix. Ghosal, S., Chauhan, R. P. S, and Srivastava, R. S., 1974. *Phytochemistry,* 13, 1933-1936.
x. Horii, Z., Ohkawa, K., Kim, S. W. and Momose, T. 1971. *Chem. Pharm. Bull.,* 19, 535-537.

The invention claimed is:

1. A process for the production of a substance or composition for the therapeutic or prophylactic treatment of erectile dysfunction or the enhancement of libido in a male human or animal subject, the process comprising the step of formulating the substance or composition from at least one of plant material and an extract of plant material of at least one plant species of the Genus *Monsonia* the material and the extract including at least one compound selected from 9-(1',3'-benzodioxol-5'-yl)-4,5,6,7-tetramethoxynaphtho[2,3-c]furan-1 (3H)-one (Compound 3),
9-(3',4'-dimethoxyphenyl)-4-hydroxy-6,7-methylenedioxynaphtho[2,3-c]furan-1(3H)-one (Compound 5),
3-(1',3'-benzodioxol-5'-ylmethylene)-4-(3",4"-dimethoxybenzyl)dihydrofuran-2(5H)-one (Compound 6), and
4-(3',4'-dimethoxyphenyl)-9-methoxy-6,7-methylenedioxynaphtho[2,3-c]furan-1(3H)-one (Compound 7).

2. A process as claimed in claim 1, in which the extract is selected from organic and aqueous extracts.

3. A process as claimed in claim 2, in which the extract is selected from organic extracts produced by extraction of plant material with an organic solvent selected from the group consisting of diethyl ether, isopropyl ether, methanol, ethanol, chloroform, dichloromethane, ethyl acetate, hexane and suitable mixtures of two or more thereof or mixtures thereof with water and aqueous extracts produced by extraction of plant material with water.

4. A process as claimed in claim 2, in which the extract is an extract produced by extraction of plant material with a supercritical fluid.

5. A process as claimed in claim 4, in which the supercritical fluid is supercritical carbon dioxide.

6. A method for the therapeutic or prophylactic treatment of erectile dysfunction or the enhancement of libido in the male human or animal body, the method comprising administering to a male human or animal subject an effective amount of a substance or composition comprising a formulation of at least one of plant material, and an extract of plant material of at least one plant species of the Genus *Monsonia*.

7. The method as claimed in claim 6, in which the plant is *M. angustifolia*.

8. The method as claimed in claim 6, in which the extract is selected from organic and aqueous extracts.

9. The method as claimed in claim 8, in which the extract is selected from organic extracts produced by extraction of plant material with an organic solvent selected from the group consisting of diethyl ether, isopropyl ether, methanol, ethanol, chloroform, dichloromethane, ethyl acetate, hexane and suitable mixtures of two or more thereof or mixtures thereof with water and aqueous extracts produced by extraction of plant material with water.

10. The method as claimed in claim 8 in which the extract is an extract produced by extraction of plant material with a supercritical fluid.

11. The method as claimed in claim 10, in which the supercritical fluid is supercritical carbon dioxide.

12. A method for the treatment by therapy or prophylaxis of erectile dysfunction or the enhancement of libido in a male human or animal subject, the method comprising administering to a male human or animal subject an effective amount of at least one compound selected from 9-(1',3'-benzodioxol-5'-yl)-4,5,6,7-tetramethoxynaphtho[2,3-c]furan-1(3H)-one (Compound 3), 9-(3',4'-dimethoxyphenyl)-4-hydroxy-6,7-methylene-dioxynaphtho[2,3-c]furan-1(3H)-one (Compound 5), 3-(1',3'-benzodioxol-5'-ylmethylene)-4-(3",4"-dimethoxybenzyl)dihydrofuran-2(5H)-one (Compound 6), and 4-(3',4'-dimethoxyphenyl)-9-methoxy-6,7-methylene-dioxynaphtho[2,3-c]furan-1(3H)-one (Compound 7).

13. A pharmaceutical composition for the therapeutic or prophylactic treatment of erectile dysfunction or the enhancement of libido in the male human or animal body, the composition comprising a formulation of at least one of plant material, and an extract of plant material of at least one plant species of the Genus *Monsonia* the material and the extract including at least one compound selected from 9-(1',3'-benzodioxol-5'-yl)-4,5,6,7-tetramethoxynaphtho[2,3-c]furan-1(3H)-one (Compound 3), 9-(3',4'-dimethoxyphenyl)-4-hydroxy-6,7-methylene-dioxynaphtho[2,3-c]furan-1(3H)-one (Compound 5), 3-(1',3'-benzodioxol-5'-ylmethylene)-4-(3",4"-dimethoxybenzyl)dihydrofuran-2(5H)-one (Compound 6), and 4-(3',4'-dimethoxyphenyl)-9-methoxy-6,7-methylene-dioxynaphtho[2,3-c]furan-1(3H)-one (Compound 7).

14. A pharmaceutical composition for the therapeutic or prophylactic treatment of erectile dysfunction or the enhancement of libido in the male human or animal body, the composition comprising a formulation of at least one of plant material, and an extract of plant material, in which the plant species is *M. angustifolia*.

15. A pharmaceutical composition as claimed in claim 13, in which the extract is selected from organic and aqueous extracts.

16. A pharmaceutical composition as claimed in claim 15, in which the extract is selected from organic extracts produced by extraction of plant material with an organic solvent selected from the group consisting of diethyl ether, isopropyl ether, methanol, ethanol, chloroform, dichloromethane, ethyl acetate, hexane and suitable mixtures of two or more thereof or mixtures thereof with water and aqueous extracts produced by extraction of plant material with water.

17. A pharmaceutical composition as claimed in claim 15, in which the extract is an organic extract produced by extraction of plant material with a supercritical fluid.

18. A pharmaceutical composition as claimed in claim 17, in which the supercritical fluid is supercritical carbon dioxide.

19. A pharmaceutical composition for the treatment by therapy or prophylaxis of erectile dysfunction or the enhancement of libido in a male human or animal subject, the composition including at least one compound selected from 9-(1',3'-benzodioxol-5'-yl)-4,5,6,7-tetramethoxynaphtho[2,3-c]furan-1(3H)-one (Compound 3), 9-(3',4'-dimethoxyphenyl)-4-hydroxy-6,7-methylene-dioxynaphtho[2,3-c]furan-1(3H)-one (Compound 5), 3-(1',3'-benzodioxol-5'-ylmethylene)-4-(3",4"-dimethoxybenzyl)dihydrofuran-2(5H)-one (Compound 6), and 4-(3',4'-dimethoxyphenyl)-9-methoxy-6,7-methylene-dioxynaphtho[2,3-c]furan-1(3H)-one (Compound 7).

20. A process for the production of a substance or composition for the therapeutic or prophylactic treatment of erectile dysfunction or the enhancement of libido in a male human or animal subject, the process comprising the step of formulating the substance or composition from at least one of plant material and an extract of plant material in which the plant is *M. angustifolia*.

\* \* \* \* \*

UNITED STATES PATENT AND TRADEMARK OFFICE
CERTIFICATE OF CORRECTION

PATENT NO. : 8,609,151 B2
APPLICATION NO. : 12/302086
DATED : December 17, 2013
INVENTOR(S) : Fouche et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1276 days.

Signed and Sealed this

Twenty-second Day of September, 2015

Michelle K. Lee
*Director of the United States Patent and Trademark Office*